United States Patent [19]

Chwalisz et al.

[11] Patent Number: 4,870,067
[45] Date of Patent: Sep. 26, 1989

[54] OXYTOCINS AND ANTIGESTAGENS IN COMBINATION FOR INDUCTION OF BIRTH

[75] Inventors: Krzsysztof Chwalisz; Sybille Beier; Walter Elger; Guenter Neef, all of Berlin, Fed. Rep. of Germany

[73] Assignee: Schering Aktiengesellschaft, Berlin and Bergkamen, Fed. Rep. of Germany

[21] Appl. No.: 904,133

[22] Filed: Sep. 5, 1986

Related U.S. Application Data

[63] Continuation-in-part of Ser. No. 660,358, Oct. 12, 1984, Pat. No. 4,626,531.

[30] Foreign Application Priority Data

Sep. 5, 1985 [DE] Fed. Rep. of Germany ....... 3531903

[51] Int. Cl.$^4$ ............................................. A61K 31/56
[52] U.S. Cl. .................................... 514/171; 514/935
[58] Field of Search ......................................... 514/171

[56] References Cited

U.S. PATENT DOCUMENTS

| | | | |
|---|---|---|---|
| 4,160,027 | 7/1979 | Christiansen | 540/23 |
| 4,609,651 | 9/1986 | Rohde et al. | 540/36 |
| 4,626,531 | 12/1986 | Elger et al. | 514/171 |

FOREIGN PATENT DOCUMENTS

0184471  6/1986  European Pat. Off. .

OTHER PUBLICATIONS

The Merck Index, 10th Ed. (1983), #6849 Oxytocin.

*Primary Examiner*—Douglas W. Robinson
*Assistant Examiner*—Joseph A. Lipovsky
*Attorney, Agent, or Firm*—Millen, White & Zelano

[57] ABSTRACT

A combination product contains oxytocin and/or an oxytocin analog and an antigestagen for induction of birth.

20 Claims, 1 Drawing Sheet

OXYTOCINS AND ANTIGESTAGENS IN COMBINATION FOR INDUCTION OF BIRTH

CROSS-REFERENCE TO RELATED APPLICATION

This application is a continuation-in-part application of commonly assigned U.S. Ser. No. 660,358, filed Oct. 12, 1984, now U.S. Pat. No. 4,626,531, which entire disclosure is incorporated by reference herein.

BACKGROUND OF THE INVENTION

This invention relates to a combination product containing oxytocin and/or an oxytocin analog (Ox) and an antigestagen (AG) for combined use in induction of birth.

Oxytocin is conventionally used as a labor inducing agent to help in giving birth and for securing uterine contractions during birth. The dosage can be given individually by i.m. or s.c. injection, especially by i.v. drip feed and also by buccal application.

Whereas, originally, preparations extracted from the posterior pituary lobe were used, nowadays only synthetic preparations are on the market. (2-O-Methyltyrosine)-oxytocin is used as an oxytocin analog for induction of labor.

It is known that the capacity of oxytocin to cause uterine contractions is decisively dependent on the stage of gestation. Only towards the end of pregnancy does there exist an oxytocin sensitivity of the uterus sufficient to allow an attempt at treatment with existing methods of birth induction arising from fetal or maternal indications. However, there exists even at "term" the problem of a great variability in the effect of an oxytocin treatment.

Early use of oxytocin when the cervix is still firm and closed, for example after premature rupture of the amnion, can lead to violent contractions of the uterus. These can be very disadvantageous for the health of the child.

SUMMARY OF THE INVENTION

Accordingly, it is an object of the invention to provide a method and composition eliminating or ameliorating the foregoing disadvantages, e.g., by increasing oxytocin sensitivity.

Upon further study of the specification and appended claims, further objects and advantages of this invention will become apparent to those skilled in the art.

Investigations with the combination of an antigestagen and oxytocin have now led to the surprising discovery that the oxytocin sensitivity of the uterus can be decisively influenced by antigestagens. It has furthermore been observed, that under the influence of the antigestagen, a softening and dilation of the cervical canal occurs. According to the present findings, by use of a previously administered or accompanying antigestagen, in each stage of the applicable gestation period, it is possible to trigger labor by oxytocin and a speedy birth can be achieved. The proposed therapy will substantially shorten the duration of a birth.

Thus, this invention relates to a combination of an antigestagen (AG) and oxytocin and/or an oxytocin analog. It also relates to a method for inducing birth in a pregnant woman comprising administering an effective amount of such a combination.

As antigestagens, all compounds can be considered which possess a strong affinity for the gestagen receptor (progesterone receptor), and also show no gestagen activity of their own. Competitive progesterone antagonists which can be used include for example, but are not limited to, the following steroids:

$11\beta$-[4-(N,N-dimethylamino)phenyl]-$17\alpha$-hydroxy-$17\beta$-propinyl-4,9(10)-estradien-3-one, $11\beta$-[4-(N,N-dimethylamino)phenyl]-$17\beta$-hydroxy-18-methyl-$17\alpha$-propinyl-4,9(10)-estradien-3-one and $11\beta$-[4-(N,N-dimethylamino)-phenyl]-$17a\beta$-hydroxy-$17a\alpha$-propinyl-D-homo-4,9(10)-16-estratrien-3-one (European Patent Application No. 82400025.1—Publication No. 0 057 115), $11\beta$-methoxyphenyl-$17\beta$-hydroxy-$17\alpha$-ethynyl-4,9(10)-estradien-3-one (Steroids 37 (1981) 361–382), $11\beta$-[4-(N,N-dimethylamino)phenyl]-$17\beta$-hydroxy-$17\alpha$-(hydroxyprop-1-(Z)-enyl)-4,9(10)-estradien-3-one (European Patent Application No. 847300147.0—Publication No. 0 147 361), and especially $11\beta$-[4-(N,N-dimethylamino)phenyl]-$17\alpha$-hydroxy-$17\beta$-(3-hydroxypropyl)-$13\alpha$-methyl-4,9(10)-gonadien-3-one (European Patent Application No. 84730062.1—Publication No. 0 129 499).

Equally suitable are antigestagens which act in a manner other than by competition on the gestagen receptor. For example, the derivatives of epostane and trilostane ($4\alpha,5\alpha$-epoxy-3,$17\beta$-dihydroxy-$4\beta,17\alpha$-dimethyl-$5\alpha$-androst-2-ene-2-carbonitrile and $4\alpha,5\alpha$-epoxy-3,$11\beta$-dihydroxy-$5\alpha$-androst-2-ene-2-carbonitrile, U.S. Pat. No. 4,160,027) which inhibit the synthesis of progesterone, can be used, The antigestagens can for example be applied locally, topically, enterally or parenterally.

Examples of forms for preferred oral administration include tablets, dragees, capsules, pills, suspensions or solutions which can be prepared in conventional manner with additives and carrier used in pharmacy. For local or topical use, vaginal pessaries, vaginal gel or percutaneous systems such as skin plasters can be used for example.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acidesters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The AG and oxytocin and/or oxytocin analog can be administered as part of the same dosage unit or preferably as separate dosage units.

The antigestagens are, according to the present invention, given in amounts which lie below the amount in other respects usual for the termination of pregnancy. In general 10-200 mg of 11$\beta$-[4-(N,N-dimethylamino)-phenyl]-17$\alpha$-hydroxy-17$\beta$-(3-hydroxypropyl)-13$\alpha$-methyl-4,9(10)-gonadien-3-one per day or a biologically equivalent amount of another antigestagen are sufficient. A dosage unit contains about 2 to 200 mg of 11$\beta$-[4-(N,N-dimethylamino)phenyl]-17$\beta$-hydroxy-17$\alpha$-(3-hydroxyprop-1-(Z)-enyl)-4,9-(10)-estradien-3-one or a biologically equivalent amount of another antigestagen. The antigestagen treatment is undertaken for 1-4, preferably 1-2 days.

Oxytocin or oxytocin analogs are preferably used in their commercially conventional presentations and dosages. Thus, injection solutions contain 1-10 I.U. of oxytocin per ml, infusion solutions contain 0.5-2 I.U. of oxytocin per 100 ml and buccal tablets contain 100-300 I.U. of oxytocin citrate per tablet. For the artificial induction of labor, the effective amount differs according to the individual as is well known. Thus, the foregoing ranges are generally applicable but as a rule, due to the effect of the AG, the dosage lies below the oxytocin dosage usual conventionally, and amounts to about 0.5 to 5 I.U. of oxytocin in the form of an infusion- or injection-solution.

According to a preferred mode of operation, the two agents are administered separately and especially sequentially, i.e., antigestagen treatment is undertaken 12 to 36 hours before the oxytocin treatment. The two agents also can be coadministered.

The administration of antigestagens can be continued after administration of oxytocin is begun, but this is less preferred.

In the general case, the amount of oxytocin or oxytocin analog administered will be less than that which otherwise would be administered conventionally without the use of AG, and/or the duration of treatment of oxytocin or oxytocin analog will be shorter than the conventional duration period. Similarly, this invention extends the period during gestation when oxytocin can be administered to include periods where sensitivity to oxytocin would otherwise be too low. Typically, this invention can be utilized as early as 28th week of pregnancy. Further analogously, this invention can be utilized to lower the amount of oxytocin necessary, thereby making such treatment available to patients who otherwise would be unable to tolerate the conventional amounts of oxytocin.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Figure 1:
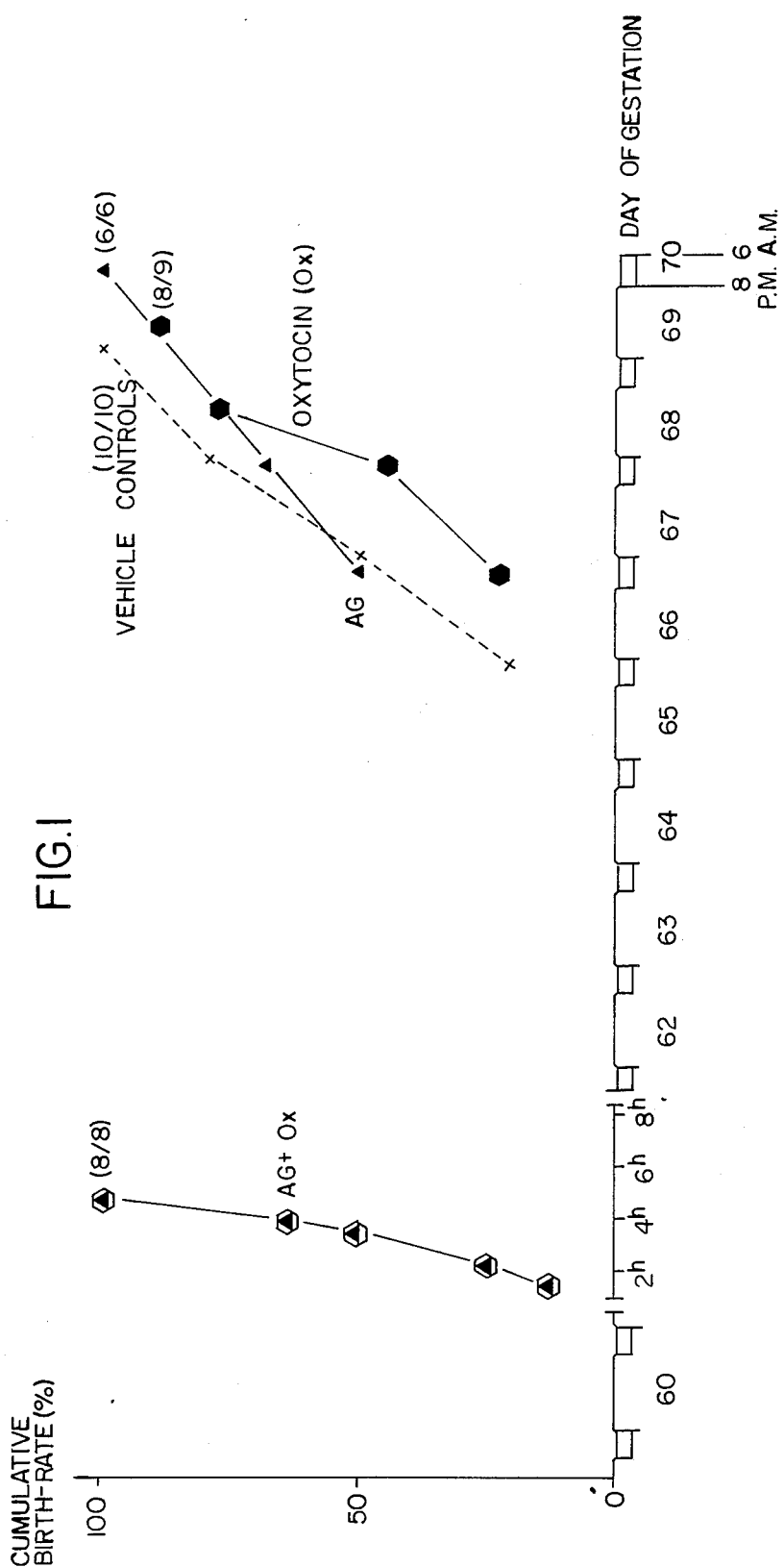
FIG. 1 summarizes in graphical form the results of the pharmacological observations on the induction of labor in guinea pigs with sequential AG/Ox-treatment, which are detailed below.

In the preceding text and the following examples, all temperatures are set forth uncorrected in degrees Celsius and all parts and percentages are by weight; unless otherwise indicated.

The following examples illustrate the pharmaceutical formulation of antigestagens.

EXAMPLE 1

Formulation of a tablet with 10 mg of 11$\beta$-[4-(N N-dimethylamino)phenyl]-17$\alpha$-hydroxy-17$\beta$-(3-hydroxypropyl)-13$\alpha$-methyl-4,9(10)gonadien-3-one for oral administration

| | |
|---|---|
| 10.0 mg | 11$\beta$-[4-(N,N—Dimethylamino)phenyl]-17$\alpha$ hydroxy-17$\beta$-(3-hydroxypropyl)-13$\alpha$-methyl-4,9(10)-gonadien-3-one |
| 140.5 mg | Lactose |
| 69.5 mg | Maize starch |
| 2.5 mg | Polyvinylpyrrolidone 25 |
| 2.0 mg | Aerosil |
| 0.5 mg | Magnesium stearate |
| 225.0 mg | |

EXAMPLE 2

Formulation of an oleaginous solution with 50 mg of 11$\beta$-[4-(N,N-dimethylamino)-phenyl]-17$\alpha$-hydroxy-17$\beta$-(3-hydroxypropyl)-13$\alpha$-methyl-4,9(10)-gonadien-3-one for parenteral administration 50 mg of the antigestagen was dissolved in 1 ml of castor oil/benzyl benzoate, in a ratio by volume of 6:4.

Pharmacological Observations

Tests:

A combination of AG and oxytocin was investigated in pregnant guinea pigs about 1 week before the natural birth term:

1. Anti-gestagen: 11β-[4-(N,N-dimethylamino)-phenyl]-17α-hydroxy-17β-(3-hydroxypropyl)-13α-methyl-4,9(10)-gonadien-3-one
   dosage/route: 0.3 mg s.c.
   Vehicle: 1 ml benzyl benzoate/castor oil (1+4)
   Frequency and time of treatment:
   One injection, 18.00 hours, day 60 post coitum.
2. Oxytocin (Syntocinon®)
   Dosage/route: 25 mU.animal/injection S.C.
   (1 mU = 1 thousandth part of an I.U.)
   Vehicle: 1 ml. commercial grade diluted with 0.9% NaCl in distilled water.
   Frequency and time of the treatment:
   9.00 hours, day 61 post coitum.
   Injections of the above mentioned dose every 60 minutes up to birth of the first fetus, maximum 6 injections (=150 mU)

Groups

1. Vehicle controls
2. Antigestagen alone
3. Oxytocin alone
4. Combination of antigestagen and oxytocin Results (See FIG. 1)

The combination of antigestagen and oxytocin led, after a few oxytocin injections, to birth in all treated 8 mother animals of this group: average number of oxytocin-injections 3.7 (=93.75 mU oxytocin), average induction-birth interval: 3.0 hours.

Other groups: with the vehicle controls, normal births at the expected time were observed, i.e., after day 65 post coitum. Oxytocin alone with the applied total dosage of 150 mU according to the test program induced no birth within the first 96 hours after commencement of the oxytocin treatment in five animals of this group. The treatment with 0.3 mg of antigestagen alone equally had no recognizable effect on the duration of birth comparable with one of the vehicle controls, although after the treatment with the antigestagen, a prematurely matured cervix and a myometrium sensitized for oxytocin may have been present.

CONCLUSION

The combination of otherwise quite inactive doses of antigestagen and oxytocin led to a fully effective procedure for the induction of labor according to a precise activation of myometrium activity after the cervix maturation.

The effect of the tested combination opens up new perspectives for the artificial induction of labor in animals and man.

The preceding examples can be repeated with similar success by substituting the generically or specifically described reactants and/or operating conditions of this invention for those used in the preceding examples From the foregoing description, one skilled in the art can easily ascertain the essential characteristics of this invention, and without departing from the spirit and scope thereof, can make various changes and modifications of the invention to adapt it to various usages and conditions.

What is claimed is:

1. A combination product useful for induction of birth comprising amounts of (a) oxytocin, an oxytocin analog or a combination thereof and (b) an antigestagen effective to induce birth.

2. A combination of claim 1, wherein components (a) and (b) are present in separate dosage units.

3. A combination product of claim 1, wherein component (a) comprises oxytocin in an amount of 1–10 I.U. per ml of an injection solution, 0.5–2 I.U. per 100 ml of an infusion solution or oxytocin citrate, in an amount of 100–300 I.U. per buccal tablet.

4. A combination of claim 3, wherein component (b) comprises about 10–200 mg of 11β-[4-(N,N-dimethylamino)-phenyl]-17α-hydroxy-17β(3-hydroxypropyl)-13α-methyl-49-(10)-gonadien-3-one or a biologically equivalent amount of another antigestagen.

5. A combination of claim 1, wherein component (b) comprises about 10–200 mg of 11β[4-(N,N-dimethylamino)phenyl]-17α-hydroxy-17β-(3-hydroxypropyl)-13α-methyl-4,9-(10)-gonadien-3-one or a biologically equivalent amount of another antigestagen.

6. A combination of claim 1, wherein component (b) comprises about 10–200 mg of 11β-[4-(N,N-dimethylamino)phenyl]-17α-hydroxy-17β-(3-hydroxypropyl)-13α-methyl-4,9-(10)-gonadien-3-one.

7. A combination of claim 6, wherein component (b) comprises about 10–200 mg of 11β[4-(N,N-dimethylamino)phenyl]-17α-hydroxy-17β-(3-hydroxypropyl)-13α-methyl-4,9-(10)-gonadien-3-one or a biologically equivalent amount of another antigestagen.

8. A combination of claim 1, wherein the antigestagen (b) is 11β-[4-(N,N-dimethylamino)phenyl]-1β-hydroxy17α-propinyl-4,9(10)-estradien-3-one, 11β-[4-(N N-dimethylamino)phenyl]-17α-hydroxy-18-methyl-17α-propinyl-4,9(10)- o estradien-3-one, 11β-[4-(N,N-dimethylamino)-phenyl]-17aβ-hydroxy-17aα-propinyl-D-homo-4,9(10)-16-estratrien-3-one, 11β-methoxyphenyl-17β-hydroxy-17α-ethynyl-4,9(10)-estradien-3-one, 11-[4-(N,N-dimethylamino)phenyl]-17β-hydroxy17α-(hydroxyprop-1-(Z)-enyl)-4,9(10)-estradien-3-one, 11β[4-(N,N-dimethylamino)phenyl]-17α-hydroxy-17β-(3-hydroxypropyl)-13α-methyl-4,9(10)-gonadien-3-one or (4α,5α-epoxy-3,17β-dihydroxy-4β,17α-dimethyl 5α-androst-2-ene-2-carbonitrile and 4α,5α-epoxy-3,17β-dihydroxy-5α-androst-2-ene-2-carbonitrile.

9. A combination product of claim 1, wherein component (a) is (2-0-methyl-tyrosine)-oxytocin.

10. A combination product of claim 1, wherein component (b) comprises about 2 to 200 mg of 11β8 4-(N,N .dimethylamino)phenyl]-17β-hydroxy-17β-(3-hydroxyprop-1 (Z)-enyl)-4,9(10)-estradien-3-one.

11. A method for inducing live birth comprising administering
   (a) an effective amount of oxytocin, an oxytocin analog or a combination thereof and
   (b) an amount of an antigestagen effective to increase oxytocin sensitivity,
   such that both compounds are simultaneously bioeffective.

12. A method of claim 11, wherein components (a) and (b) are administered separately.

13. A method of claim 12, wherein components (a) and (b) are administered sequentially, the antigestagen before component (a).

14. A method of claim 13, wherein the antigestagen is administered about 12–36 hours before component (a).

15. A method of claim 14, wherein component (a) comprises oxytocin in an amount of 1–10 I.U. per ml of an injection solution, 0.5–2 I.U. per 100 ml of an infusion solution or oxytocin citrate in an amount of 100–300 I.U. per buccal tablet.

16. A method of claim 11, wherein the antigestagen comprises 10–200 mg of 11β-[4-(N,N-dimethylaminophenyl)-17? -hydroxy-17α-(3-hydroxpropyl)-13α-methyl-4,9(10)-gonadiene-3-one or of a biologically equivalent amount of another antigestagen.

17. A method of claim 11, wherein component (b) is administered orally.

18. A method of claim 11, wherein the antigestagen is 11β-[4-(N,N-dimethylamino)phenyl]-17β-hydroxy-17α-propinyl-4,9(10) -estradien-3-one, 11β-[4-(N,N-dimethylamino)phenyl] -17β -hydroxy-18 -methyl-17α-propinyl-4,9(10)-estradien-3-one, 11β-[4-(N,N-dimethylamino)-phenyl]-17aβ-hydroxy-17aα-propinyl-D-homo-4, 9(10)-16-estradien-3-one, 11β-methoxy phenyl-17β-hydroxy-17α-ethynyl-4,9(10)-estradien-3-one, 11β-[4-(N,N-dimethylamino)phenyl]-17β-hydroxy-17? -(hydroxy-prop-1-(z)-enyl) -4,9(10)-estradiene-3-one, 11β-[4-(N,N-di-methylamino)phenyl] -17β -hydroxy-17α-(3-hydroxpropyl)-13α-methyl-4,9(I0)-gonadien-3-one or (4α,5α-epoxy-3,17β-dihydroxy-4α ,17β -dimethyl-5α -androst-2-ene-2-carbonitrile and 4α,5α-epoxy-3,17β-dihydroxy-5α-androst-2-ene-2-carbonitrile.

19. A method of increasing the sensitivity of a pregnant female to oxytocin or an oxytocin analog comprising administering to said female in whom it is desired to increase said sensitivity an effective amount of an antigestagen at the beginning of or during the induction of live birth.

20. A method of increasing the sensitivity of a pregnant female to an agent which induces contractions comprising administering to said female in whom it is desired to increase said sensitivity an effective amount of an antigestagen at the beginning of or during the induction of live birth.

* * * * *

UNITED STATES PATENT AND TRADEMARK OFFICE
CERTIFICATE OF CORRECTION

PATENT NO.  : 4,870,067

DATED       : September 26, 1989

INVENTOR(S) : KRZSYSZTOF CHWALISZ ET AL

It is certified that error appears in the above-identified patent and that said Letters Patent is hereby corrected as shown below:

Column 5, claim 1, line 68:

reads "A combination product useful for induction of"

should read -- A combination product useful for induction of live --

Column 6, claim 4, line 13:

reads "13α-methyl-49-(10)-gonadien-3-one or a biologically"

should read --13α-methyl-4,9-(10)-gonadien-3-one or a biologically--

Column 6, claim 8, line 32:

reads "dimethylamino)phenyl] -17α-hydroxy-18-methyl-17α-"

should read -- dimethylamino)phenyl] -17β-hydroxy-18-methyl-17α- --

UNITED STATES PATENT AND TRADEMARK OFFICE
CERTIFICATE OF CORRECTION

PATENT NO. : 4,870,067

DATED : September 26, 1989

INVENTOR(S) : KRZSYSZTOF CHWALISZ ET AL

It is certified that error appears in the above-identified patent and that said Letters Patent is hereby corrected as shown below:

Column 6, claim 10, line 49:

reads "dimethylamino)phenyl] -17β-hydroxy-17β-(3-hydroxy-"

should read —dimethylamino)phenyl] -17β-hydroxy-17α-(3-hydroxy- —

Column 7, claim 16, line 5:

reads "phenyl)-17?-hydroxy-17α-(3-hydroxpropyl)-13α-meth-"

should read — phenyl)-17α-hydroxy-17β-(3-hydroxypropyl)-13α-meth- —

Column 7, claim 18, line 18:

reads "[4-(N,N-dimethylamino)phenyl] -17β-hydroxy-17?-(hy-"

should read — [4-(N,N-dimethylamino)phenyl] -17β-hydroxy-17α-(hy- —

Column 8, claim 18, line 3:

reads "(4α,5α-epoxy-3,17β-dihydroxy-4α ,17β -dimethyl-5α"

should read — (4α,5α-epoxy-3,17β-dihydroxy-4β ,17α -dimethyl-5α —

Signed and Sealed this

Seventeenth Day of April, 1990

Attest:

HARRY F. MANBECK, JR.

*Attesting Officer*    *Commissioner of Patents and Trademarks*